(12) United States Patent
Marcelpoil et al.

(10) Patent No.: US 9,122,904 B2
(45) Date of Patent: Sep. 1, 2015

(54) METHOD FOR OPTIMIZATION OF QUANTITATIVE VIDEO-MICROSCOPY AND ASSOCIATED SYSTEM

(75) Inventors: Raphael Rodolphe Marcelpoil, Corenc (FR); Cedrick Rene Orny, Grenoble (FR)

(73) Assignee: TriPath Imaging, Inc., Burlington, NC (US)

( * ) Notice: Subject to any disclaimer, the term of this patent is extended or adjusted under 35 U.S.C. 154(b) by 653 days.

(21) Appl. No.: 13/444,444

(22) Filed: Apr. 11, 2012

(65) Prior Publication Data

US 2012/0262564 A1    Oct. 18, 2012

Related U.S. Application Data

(60) Provisional application No. 61/474,520, filed on Apr. 12, 2011.

(51) Int. Cl.
| | |
|---|---|
| *H04N 7/18* | (2006.01) |
| *G06K 9/00* | (2006.01) |
| *G01N 21/59* | (2006.01) |
| *G06T 7/00* | (2006.01) |

(52) U.S. Cl.
CPC ........ *G06K 9/00127* (2013.01); *G01N 21/5907* (2013.01); *G06T 7/0012* (2013.01); *G06T 2207/10016* (2013.01); *G06T 2207/10056* (2013.01); *G06T 2207/30072* (2013.01)

(58) Field of Classification Search
None
See application file for complete search history.

(56) References Cited

U.S. PATENT DOCUMENTS

| | | | |
|---|---|---|---|
| 7,065,236 | B2 | 6/2006 | Marcelpoil et al. |
| 7,133,547 | B2 | 11/2006 | Marcelpoil et al. |
| 7,602,954 | B2 | 10/2009 | Marcelpoil et al. |
| 7,826,650 | B2 | 11/2010 | Marcelpoil et al. |
| 7,989,209 | B2 | 8/2011 | Marcelpoil et al. |
| 2006/0204068 | A1* | 9/2006 | Marcelpoil et al. ........... 382/129 |
| 2007/0026525 | A1 | 2/2007 | Marcelpoil et al. |
| 2007/0053573 | A1 | 3/2007 | Rabinovich |
| 2008/0065359 | A1* | 3/2008 | Rudolph et al. .................. 703/2 |
| 2010/0054574 | A1 | 3/2010 | Marcelpoil et al. |
| 2010/0061618 | A1 | 3/2010 | Marcelpoil et al. |
| 2010/0067775 | A1 | 3/2010 | Marcelpoil et al. |

FOREIGN PATENT DOCUMENTS

| | | |
|---|---|---|
| WO | WO 03/025554 A2 | 3/2003 |
| WO | WO 03/062803 A2 | 7/2003 |
| WO | WO 2006/081547 A1 | 8/2006 |

OTHER PUBLICATIONS

Keshava, Nirmal, "A Survey of Spectral Unmixing Algorithms," *Lincoln Laboratory Journal*, 2003, vol. 14(1), pp. 55-78.

* cited by examiner

*Primary Examiner* — Frederick Bailey
(74) *Attorney, Agent, or Firm* — Lerner, David, Littenberg, Krumholz & Mentlik, LLP

(57) ABSTRACT

Embodiments of the present invention are directed to a method for determining an amount of a plurality of molecular species in a sample, each molecular specie being indicated by a dye. According to one embodiment, the amount of a plurality of molecular species is determined by acquiring a plurality of images of the sample, determining an amount of each molecular specie, as indicated by a respective dye, for each pixel at each corresponding pixel location in the plurality of images, and refining the amount of a plurality of molecular species at one or more pixel locations in the plurality of images. Associated systems and computer program products are also provided.

25 Claims, 3 Drawing Sheets

METHOD FOR OPTIMIZATION OF QUANTITATIVE VIDEO-MICROSCOPY AND ASSOCIATED SYSTEM

FIELD OF THE INVENTION

The present invention relates to image analysis and, more particularly, to a method for refining quantitative video-microscopy in cellular biology and pathology applications and an associated system and computer software program product therefor.

BACKGROUND OF THE INVENTION

Effective analysis of microscopic images is essential in cellular biology and pathology, particularly for detection and quantification of genetic materials such as, for example, genes or messenger RNA, or the expression of this genetic information in the form of proteins such as through, for example, gene amplification, gene deletion, gene mutation, messenger RNA molecule quantification, or protein expression analyses. Gene amplification is the presence of too many copies of the same gene in one cell, wherein a cell usually contains two copies, otherwise known as alleles, of the same gene. Gene deletion indicates that less than two copies of a gene can be found in a cell. Gene mutation indicates the presence of incomplete or non-functional genes. Messenger RNAs (mRNA) are molecules of genetic information, synthesized from a gene reading process, that serve as templates for protein synthesis. Protein expression is the production of a given protein by a cell. If the gene coding for the given protein, determined from a protein expression process, is enhanced or excess copies of the gene or mRNA are present, the protein may be over-expressed. Conversely, if the gene coding is suppressed or absent, the protein may be under-expressed or absent.

Normal cellular behaviors are precisely controlled by molecular mechanisms involving a large number of proteins, mRNAs, and genes. Gene amplification, gene deletion, and gene mutation are known to have a prominent role in abnormal cellular behaviors through abnormal protein expression. The range of cellular behaviors of concern includes behaviors as diverse as, for example, proliferation or differentiation regulation. Therefore, effective detection and quantification in gene amplification, deletion and mutation, mRNA quantification, or protein expression analyses is necessary in order to facilitate useful research, diagnostic and prognostic tools.

There are numerous laboratory techniques directed to detection and quantification in gene amplification, deletion and mutation, mRNA quantification, or protein expression analyses. For example, such techniques include Western, Northern and Southern blots, polymerase chain reaction ("PCR"), enzyme-linked immunoseparation assay ("ELISA"), and comparative genomic hybridization ("CGH") techniques. However, microscopy is routinely utilized because it is an informative technique, allowing rapid investigations at the cellular and sub-cellular levels while capable of being expeditiously implemented at a relatively low cost.

When microscopy is the chosen laboratory technique, the biological samples must first undergo specific detection and revelation preparations. Once the samples are prepared, a human expert typically analyzes the samples with a microscope alone in a qualitative study, or with a microscope coupled to a camera and a computer in a quantitative and generally standardized study. In some instances, the microscope may be configured for fully automatic analysis, wherein the microscope is automated with a motorized stage and focus, motorized objective changers, automatic light intensity controls and the like.

The preparation of the samples for detection may involve different types of preparation techniques that are suited to microscopic imaging analysis, such as, for example, hybridization-based and immunolabeling-based preparation techniques. Such detection techniques may be coupled with appropriate revelation techniques, such as, for example, fluorescence-based and visible color reaction-based techniques.

In Situ Hybridization ("ISH") and Fluorescent In Situ Hybridization ("FISH") are detection and revelation techniques used, for example, for detection and quantification in genetic information amplification and mutation analyses. Both ISH and FISH can be applied to histological or cytological samples. These techniques use specific complementary probes for recognizing corresponding precise sequences. Depending on the technique used, the specific probe may include a chemical (ISH) marker or a fluorescent (FISH) marker, wherein the samples are then analyzed using a transmission microscope or a fluorescence microscope, respectively. The use of a chemical marker or a fluorescent marker depends on the goal of the user, each type of marker having corresponding advantages over the other in particular instances.

In protein expression analyses, immunohistochemistry ("IHC") and immunocytochemistry ("ICC") techniques, for example, may be used. IHC is the application of immunochemistry to tissue sections, whereas ICC is the application of immunochemistry to cultured cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody.

In both hybridization and immunolabeling studies, chromogens of different colors are used to distinguish among the different markers. However, the maximum number of markers that may be used in a study is restricted by several factors. For example, the spectral overlapping of the colors used to reveal the respective markers may be a limiting factor because dyes may absorb throughout a large portion of the visible spectrum. Accordingly, the higher the number of dyes involved in a study, the higher the risk of spectral overlapping. Further, the spectral resolution of the acquisition device may be a limiting factor and the minimal color shift that the device is able to detect must be considered.

In addition, immunochemistry, as well as chemistry in ISH, are generally considered to exhibit poor sensitivity when quantification of a marker must be achieved.

However, the quantification accuracy of these techniques may be dependent upon several factors. For instance, the type of reaction used may play a role in the accuracy of the technique since the linearity of the relationship between ligand concentration and the degree of the immunochemical staining reaction may strongly depend on the reaction type. More particularly, for example, a peroxidase/anti-peroxidase method may be more linear than a biotin-avidin method. The cellular localization of the markers may also affect accuracy where, for example, if membrane and nuclear markers spatially overlap, the resulting color is a mixture of the respective colors. Accordingly, since the corresponding quantification is subjective, the accuracy of the determination may be affected. In addition, a calibration standard such as, for example, cells with known features, gels with given concentrations of the marker, or the like, may be required where a developed analysis model is applied to a new and different case. Staining kits are generally available which incorporate calibration standards. However, the calibration standard is usually only applicable to a particular specimen, such as a specific cell or a structure of a specific type which is known to exhibit constant features with respect to the standard, and may be of limited utility when applied to a sample of a different nature.

Overall, the described "colorimetric" studies present sample analysis information in color and facilitate processing and quantification of the information to thereby help to provide a diagnosis or to form a prognosis of the particular case. For illustration, the detection and quantification of the HER2 protein expression and/or gene amplification may be assessed by different approaches used in quantitative microscopy. HER2 is a membrane protein that has been shown to have a diagnostic and prognostic significance in metastatic breast cancer. Because HER2 positive patients were shown to be more sensitive to treatments including Herceptin® (a target treatment developed by Genentech), the definition of the HER2 status of metastatic breast cancers has been proven to be of first importance in the choice of the appropriate treatment protocol. This definition of the HER2 status was based on a study of samples treated with either hybridization (FISH, ISH) or immunolabeling (IHC) techniques.

In such studies, using FISH with, for example, an FDA approved kit such as PathVysion® produced by Vysis, requires an image analysis protocol for counting the number of copies of the HER2 gene present in every cell. In a normal case, two copies of the gene are found in each cell, whereas more than three copies of the gene in a cell indicate that the gene is amplified. Alternatively, using IHC with, for example, an FDA approved kit such as Herceptest® produced by Dako, requires an image analysis protocol that classified the cases into four categories depending on the intensity and localization of the HER2 specific membrane staining Current studies tend to show that these two investigation techniques (hybridization and immunolabeling) may be complementary and may help pathologists in tumor sub-type diagnosis when combined.

However, such colorimetry studies require extensive sample preparation and procedure control. Thus, when disposing of adapted staining protocols, it is critical to be able to verify that the staining for each sample matches the particular model used in the image acquisition and processing device such that useful and accurate results are obtained from the gathered information. Otherwise, the analysis may have to be repeated, starting again from the sample preparation stage, thereby possibly resulting in a costly and time-consuming process.

In a typical microscopy device based on image acquisition and processing, the magnified image of the sample must first be captured and digitized with a camera. Generally, charge coupled device (CCD) digital cameras are used in either light or fluorescence quantitative microscopy. Excluding spectrophotometers, two different techniques are generally used to perform such colorimetric microscopy studies. In one technique, a black and white (BW) CCD camera may be used. In such an instance, a gray level image of the sample is obtained, corresponding to a monochromatic light having a wavelength specific to the staining of the sample to be analyzed. The specific wavelength of light is obtained either by filtering a white source light via a specific narrow bandwidth filter, or by directly controlling the wavelength of the light source, using either manual or electronic controls. Images of the sample, showing the spectral response of the sample at different wavelengths, are individually captured in sequential order to facilitate the analysis. When multiple scenes or fields of view are analyzed, the typical protocol is to automate the sequence in a batch mode to conserve processing time.

According to a second technique, a color CCD digital camera is used, wherein three gray level images of the sample are simultaneously captured and obtained. Each gray level image corresponds to the respective Red, Green and Blue channel (RGB) of the color CCD camera. The images are then analyzed directly in the RGB color space by restricting the analysis to pixels located in a specific region of the RGB cube, the specific region also including pixels from a corresponding training database. Alternatively, the images are analyzed, after mathematical transform of the RGB color space, in one of the many color spaces defined by the CIE (International Commission on Illumination) such as, for example, an HLS (Hue, Luminance or Saturation) space. Alternatively, some camera manufacturers produce specific CCD cameras, wherein narrow bandwidth filters for targeting specific wavelengths may replace the usual Red, Green and Blue filters. In such an instance, the camera allows a fast image capture of the three spectral components of a scene in a parallel manner. However, cameras modified in this manner may be restricted to specific spectral analysis parameters because the filters cannot be changed and therefore cannot be adapted to address a unique dye combination used for the sample. Thus, the second technique generally relies upon either the detection of contrast between the specie/species of interest and the remainder of the sample or the analysis of the sample over a narrow bandwidth.

Accordingly, techniques used in colorimetric analyses of prepared samples are of limited use in the detection and quantification of species of interest due to several factors such as, for example, spectral overlapping, mixing of colors due to spatially overlapping of membrane, cytoplasmic, and nuclear markers, chromatic aberrations in the optical path, limited spectral resolution of the acquisition device, calibration particularities, subjectivity of the detection and quantification process, and inconsistencies between human operators. The image processing portion of colorimetric analysis techniques has historically been directed to the subjective detection of contrast within the prepared sample or to a complex and voluminous analysis of the sample at various specific wavelengths of light using a combination of light sources and filters. Therefore, there exists a need for a refinement of colorimetric analysis techniques that overcomes detection and quantification limitations found in prior art analysis techniques. Such a refinement should also be capable of providing high quality data, comprising the necessary analysis information about the sample, while reducing subjectivity and inconsistency in the sample analysis.

SUMMARY OF THE INVENTION

The above and other needs are met by the present invention which, in one embodiment, provides a method for determining an amount of a plurality of molecular species in a sample, each molecular specie being indicated by a dye. The method generally includes acquiring a plurality of images of the sample. The images may be acquired by an image-acquisition device, such as a camera and/or a scanner, in a video-microscopy system. The method includes determining an amount of each molecular specie, as indicated by a respective dye, for each pixel at each corresponding pixel location in the plurality of images and refining the amount of a plurality of molecular species at one or more pixel locations in the plurality of images.

According to aspects of the invention, the amount of each molecular specie may be determined using a chromogen separation technique. Such a technique includes determining an optical density of the sample in each pixel at each corresponding pixel location in the plurality of images. A corresponding optical density matrix is thereafter formed for that pixel and multiplied by the inverse of a relative absorption coefficient matrix so as to form a resultant matrix for the pixel. The relative absorption coefficient matrix comprises a relative absorption coefficient for each dye, independently of the sample, in each of the wavelengths. The resultant matrix thus comprises an unrefined amount of each molecular specie, as indicated by the respective dye for that pixel.

The method further provides refining the amount of a plurality of molecular specie at one or more pixel locations. According to one aspect, refining may include determining each molecular specie comprising a significant concentration and refining the concentration for a plurality of molecular species having a significant concentration at one or more pixel locations. Refinement of the amount of a plurality of molecular species may further include determining a number of subsets of wavelength filter combinations and testing each of the subsets of wavelength filter combinations according to an optimality factor. Each subset of wavelength filter combinations may include a number of wavelength filters equal to the number of dye concentrations that are present in the sample in a significant concentration.

In one embodiment, testing each of the subsets of wavelength filter combinations comprises multiplying a hypervolume of an absorption coefficient matrix and a hypervolume of a transpose of the absorption coefficient matrix that is specific to a particular subset of wavelength filter combinations. According to one embodiment, multiplication of the hypervolumes comprises multiplying a Cayley-Menger Determinant of an absorption coefficient matrix and a Cayley-Menger Determinant of a transpose of the absorption coefficient matrix that is specific to a particular subset of wavelength filter combinations. The subset of wavelength filters that produces the maximum product comprises the optimal wavelength filter combination. Accordingly, the method may further include determining an optimized optical density matrix for each pixel location, determining an optimized relative absorption coefficient matrix, and multiplying the optimized optical density matrix by an inverse of the optimized relative absorption coefficient matrix so as to form a resultant matrix comprising the optimized dye concentrations for each pixel location, the optimized dye concentrations comprising the amount of each molecular specie, as indicated by the respective dye.

Another advantageous aspect of the present invention comprises a video-microscopy system for determining an amount of a plurality of molecular species in a sample, each molecular specie being indicated by a dye, from a plurality of images of the sample. According to one embodiment, the system comprises an image acquisition device configured to capture a plurality of magnified digital images of the sample and a processor device in communication with the image acquisition device. The processor device may be configured to determine an amount of each molecular specie, as indicated by a respective dye, for each pixel at each corresponding pixel location in the plurality of images and refine the amount of a plurality of molecular species at one ore more pixel locations in the plurality of images. According to one aspect, the image-acquisition device may include a plurality of filters wherein each filter corresponds to a particular wavelength of light.

The processor device may be further configured to determine an optical density of the sample in each of a plurality of wavelengths and for a pixel in the image, so as to form a corresponding optical density matrix for each pixel at each corresponding pixel location. The processor device may also be configured to determine a relative absorption coefficient matrix for the dye indicating each molecular specie, independently of the sample and in each of the plurality of wavelengths, so as to form a corresponding relative absorption coefficient matrix. In addition, the processor device may be configured to multiply the optical density matrix by an inverse of the relative absorption coefficient matrix so as to form a dye concentration matrix for each pixel location. The processor device is further configured to determine a number of subset of wavelength filter combinations, test each subset of wavelength filter combinations, and determine an optimal wavelength filter combination.

In one embodiment, the processor device is configured to determine a hypervolume of an absorption coefficient matrix specific to a particular combination of wavelength filters and determine a hypervolume of a transpose of the absorption coefficient matrix specific to a particular wavelength filter combination. Further, the processor device may be configured to determine the Cayley-Menger Determinants of the an absorption coefficient matrix and a transpose of the absorption coefficient matrix. Additionally, the processor device may be configured to maximize the product of the Cayley-Menger Determinants of the absorption coefficient matrix and the transpose of the absorption coefficient matrix.

Still another advantageous aspect of the present invention comprises a computer software program product configured to be executable on a computer device for determining an amount of a plurality of molecular species in a sample, each molecular specie indicated by a dye. The computer program product comprises an executable potion for acquiring a plurality of images of the sample, an executable portion for determining an amount of each molecular specie, as indicated by a respective dye, fore each pixel at each corresponding pixel location in the plurality of images, and an executable portion for refining the amount of a plurality of molecular species at one or more pixel locations in the plurality of images.

Thus, embodiments of the present invention comprise a refined colorimetric analysis technique for prepared samples that may provide effective detection and quantification of species of interest that overcomes limiting factors of prior art technologies, such as errors in dye concentration estimations due to noise fluctuations and/or global noise. Embodiments of the present invention may further provide more accurate estimations of dye concentrations of each corresponding pixel location of the plurality of images of the sample so as to optimize the amounts of those molecular species indicated in the images.

BRIEF DESCRIPTION OF THE DRAWINGS

Figure 1:
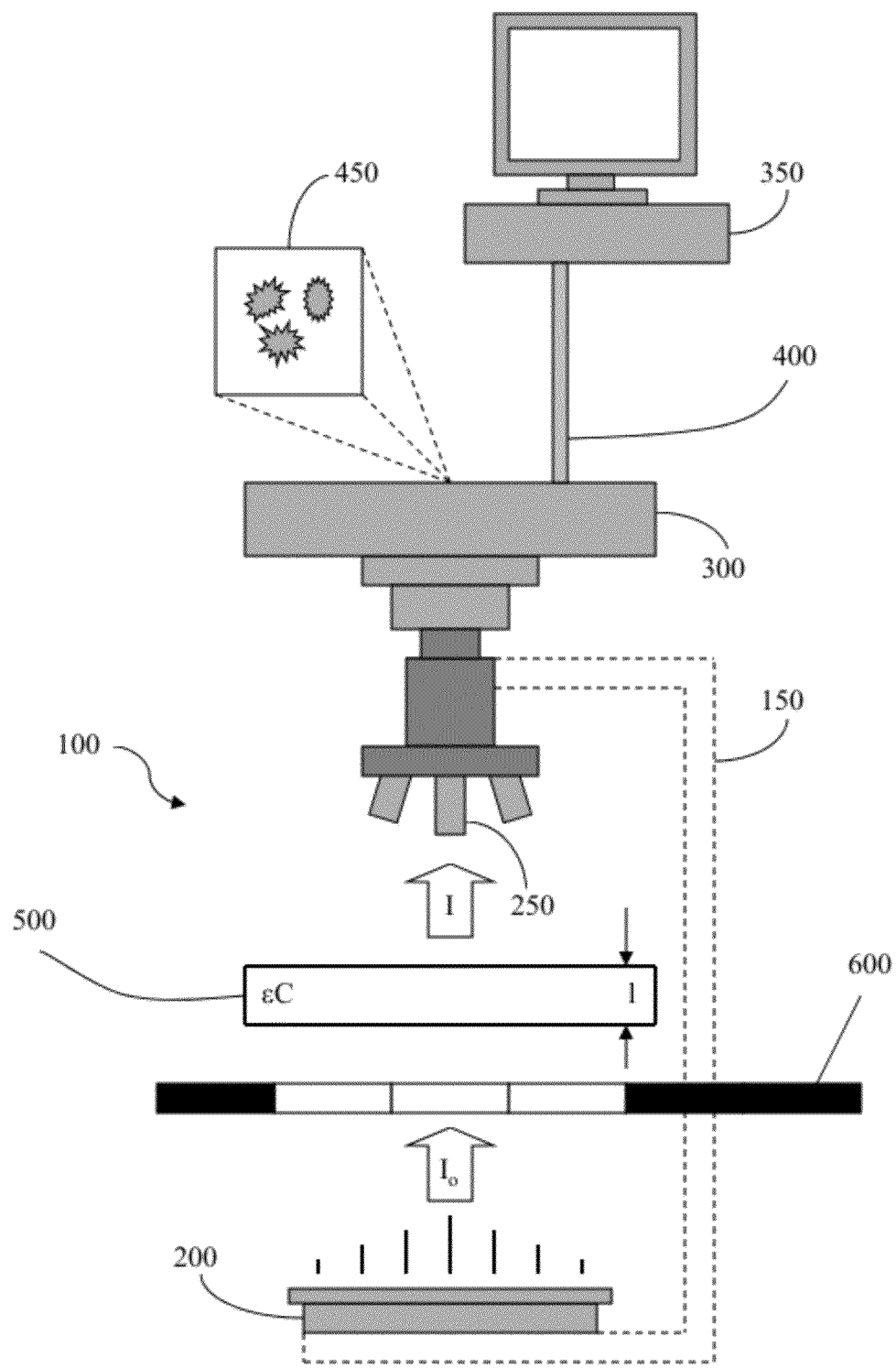
Figure 2:
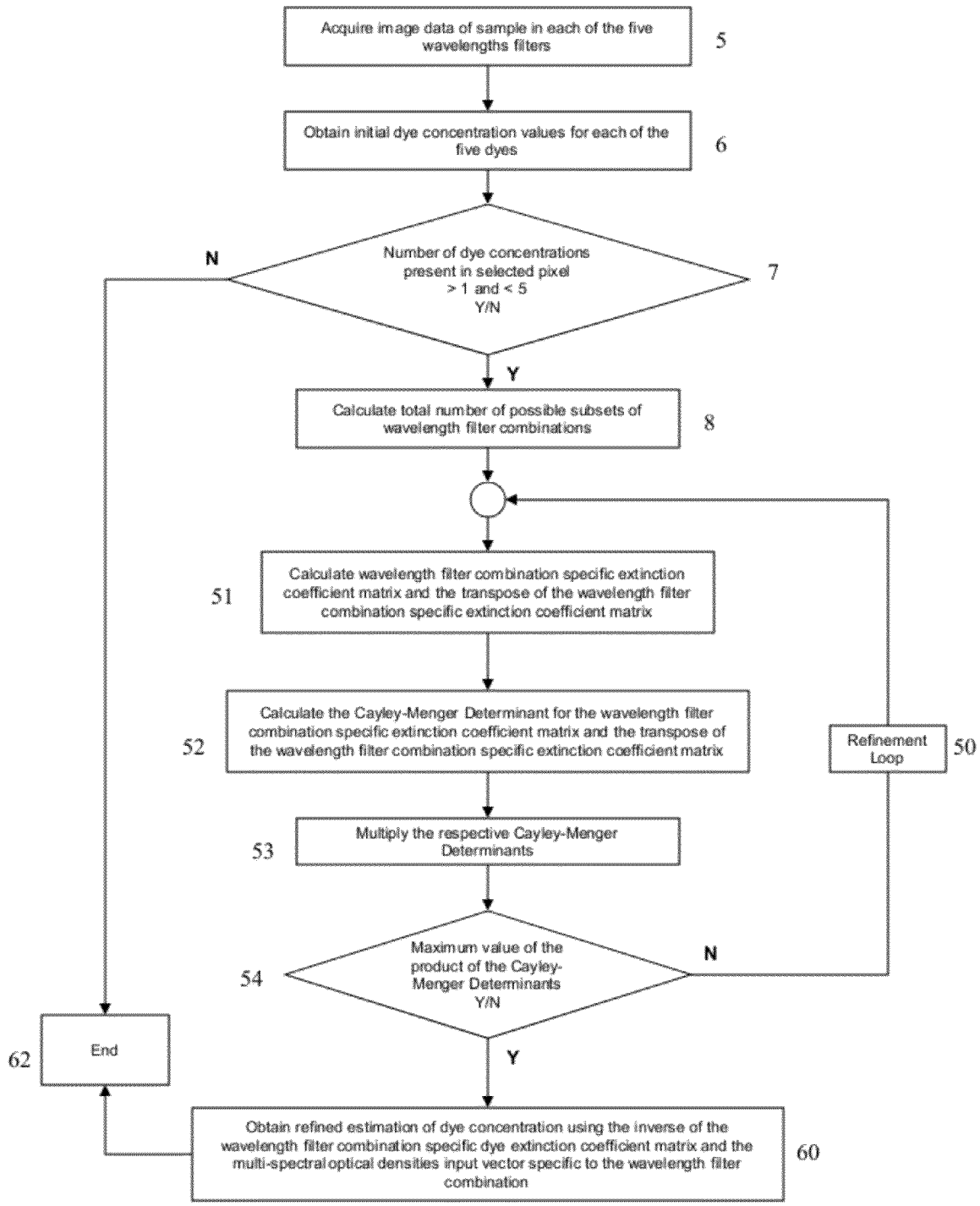
Figure 3:
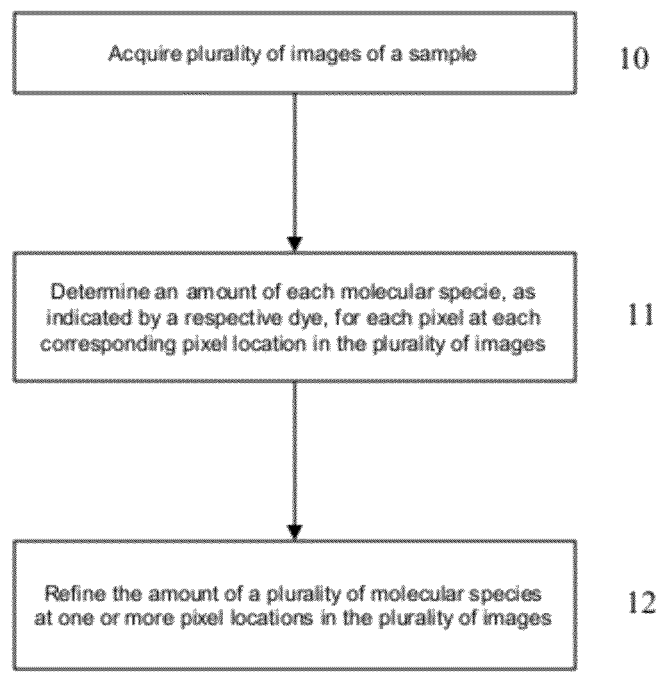

Having thus described the invention in general terms, reference will now be made to the accompanying drawings, which are not necessarily drawn to scale, and wherein:

FIG. 1 is a general schematic representation of a quantitative video-microscopy system according to one embodiment of the present invention;

FIG. 2 is a flowchart for determining a refined amount of a plurality of molecular species in a sample according to one embodiment of the present invention; and FIG. 3 is a flowchart for determining a refined amount of a plurality of molecular species in a sample according to one embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the present invention are generally directed to systems and methods for determining and refining the amount (e.g., concentration) of a plurality of molecular specie in a sample, the molecular specie being indicated by a dye, as shown in FIG. 3. The amount of the molecular specie is determined by analyzing images of the sample that are captured using an image acquisition device 10, such as a camera or a scanner, in a video-microscopy system. According to one embodiment of the invention, the system may be configured so as to be capable of detecting one or more particular dyes, each dye corresponding to a particular spectral signature, so as to determine the amount of a molecular specie in each pixel at each pixel location in the images 11. In one embodiment, the dyes that are determined to be in significant amounts at one or more pixel locations are refined so as to optimize the amount of those molecular species having a significant concentration in the sample 12. Thus, embodiments of the present invention may provide advantages over the prior art, such as reducing the errors in the estimations of the dye concentration estimations due to noise fluctuation.

According to one embodiment of the present invention, the analysis of the sample may be used to quantify melastatin staining in both normal melanocyte nuclei (melanocytes from the basal layer of epithelial cells), considered as reference nuclei, and abnormal melanocyte nuclei (melanocytes from tumor foci). The results of such a quantitative analysis indicate whether the gene is either downregulated or normally expressed in the abnormal nuclei. However, the efficiency of the quantitative analysis heavily depends upon the image analysis methodology, which must consider and perform segmentation of the melanocyte nuclei, as well as colorimetric analysis of the specific dyes used in the protocol.

A plurality of chromogens may be present in a histological or cytological sample such as, for example, one or more markers (e.g., Brown DAB or BCIP-NBT), one or more morphological counterstains (e.g., Nuclear Fast Red-NFR, Haematoxylin, Eosin, Light Green SF, Orange G), and one or more natural pigments (e.g., melanin) All of the chromogens are typically taken into account for analyzing the sample, and embodiments of the present invention provide techniques for analyzing the sample given each of the chromogens, on a per pixel basis, to quantify the amount of one or more molecular specie in the sample. For example, the cytological test based on Papanicolaou stain is a multichromatic staining procedure that would contain 4 different dyes: haematoxylin, Orange G, Eosin Y and Light Green SF.

The platform for the evaluation of biological samples via image analysis is increasingly shifting from a general-purpose image analyzer to a more, and often highly, specialized dedicated "pathology workstation." Such workstations are typically designed to facilitate routine work, often combining many of the tools needed to provide a pathologist with the necessary information to determine the best possible results. One example of such a workstation is illustrated in FIG. 1 as a quantitative video-microscopy system, indicated by the numeral 100, according to one embodiment of the present invention. The system 100 generally comprises a microscope 150 having a light source 200 and a magnifying objective 250, a plurality of filters 600, a camera 300, a computer device 350, and a data transmission link 400 between the camera 300 and the computer device 350. The microscope 150 may comprise, for example, an Axioplan (or Axiovert) microscope produced by ZEISS of Germany or a similar microscope having a bright field light source. The camera 300 operably engages the microscope 150 and, in one embodiment, comprises a black-and-white camera, such as, for instance the prosilica GE1910 from Allied Vision Technologies. Typically, such a camera 300 also includes an associated frame grabber (not shown) to facilitate image capture, both the camera 300 and associated frame grabber being referred to herein as the "camera 300" for convenience. In some instances, both camera 300 and microscope 150 may be replaced by, for example, a black-and-white linear flat scanner and a controlled illumination source. Note that, though different configurations of the necessary system 100 are contemplated by the present invention, the present invention will be described herein in terms of a camera 300 and associated microscope 150. Accordingly, one skilled in the art will understand and appreciate the capabilities and methodologies associated with these different configurations for accomplishing the present invention as detailed herein. Further, although the present embodiment is disclosed as a camera, it is understood that the camera may be any image acquisition device, such as a camera, scanner, or any device configured to capture a plurality of images. The image acquisition system is capable of capturing low and/or high resolution images at any desired magnification, various regions of interest, and within various fields of view that may correspond to all or a portion of the sample or the slide.

The camera 300 is generally configured to capture a plurality of images 450 of a sample 500 through the magnifying objective 250 (where a flat scanner is used, the image 450 is captured through internal lenses), wherein the images 450 may further comprise a digital image having corresponding image data (collectively referred to herein as "the image 450"). According to one embodiment, the sample is placed on a slide for analysis by the camera 300. The filters 600 filter light from light source 200, and during operation of the system 100, multiple images of the sample 500 are taken using different filters, the differing filters provided for by a filter wheel or other filtering device as known to those skilled in the art. According to one embodiment, each wavelength corresponds to a respective dye of interest that may be present in the images. In one embodiment, the filters employed may correspond to the wavelengths of 460 nm, 490 nm, 520 nm, 570 nm, and 630nm. Accordingly, the images 450 are generally captured individually, wherein each image corresponds to an individual wavelength filtered image of the field of view. The data transmission link 400 is configured so as to be capable of transmitting the image 450 to the computer device 350, wherein the computer device 350 is further configured to be capable of analyzing the image 450 with respect to each of the wavelengths. One skilled in the art will appreciate the computer device 350 may be any sort of processor device or processing element configured to communicate with the image acquisition system and is further configured to analyze a plurality of images as described herein.

According to a particularly advantageous aspect of the present invention, the system 100 is configured to analyze the sample in accordance with the Lambert-Beer law. The Lambert-Beer law generally describes a proportionality that can be observed between the concentration of molecules in a solution (the concentration of the "molecular specie" or the "sample") and the light intensity measured through the solution. The Lambert-Beer law is typically expressed as:

$$OD = \epsilon \cdot l \cdot C \quad (1)$$

where OD is the optical density of the solution, $\epsilon$ is a proportionality constant called the molar extinction or absorption coefficient, 1 is the thickness of the sample, and C is the concentration of the molecular specie. The absorption coefficient $\epsilon$ is specific to the molecular specie and is typically expressed in units of $L \cdot mol^{-1} \cdot cm^{-1}$.

This proportionality relationship defined by the Lambert-Beer law has been verified under the several conditions including, for example, monochromatic light illuminating the sample, low molecular concentration within the sample, generally no fluorescence or light response heterogeneity (negligible fluorescence and diffusion) of the sample, and lack of chemical photosensitivity of the sample. Further, another requirement for an analysis according to the Lambert-Beer law includes, for instance, correct Köhler illumination of the sample under the microscope. Köhler illumination is available with many modern microscopes, providing an even illumination of the sample in the image plane and allowing for effective contrast control. Köhler illumination is critical for certain processes such as, for example, densitometry analysis. Correct Köhler illumination is typically provided by, for example, a two-stage illuminating system for the microscope in which the source is imaged in the aperture of the sub-stage condenser by an auxiliary condenser. The sub-stage condenser, in turn, forms an image of the auxiliary condenser on the object. An iris diaphragm may also be placed at each condenser, wherein the first iris controls the area of the object to be illuminated, and the second iris varies the numerical aperture of the illuminating beam.

The Lambert-Beer law has an additive property such that, if the sample comprises several light-absorbing molecular species, for example, $s_1$ and $s_2$, having respective concentrations $C_1$ and $C_2$, the OD of a sample of thickness 1 (where $l_1 = l_2 = 1$ for the sample, as indicated in the solution hereinafter) can be expressed as:

$$OD = \epsilon_1 \cdot l_1 \cdot C_1 + \epsilon_2 \cdot l_2 \cdot C_2 \quad (2)$$

This situation may occur, for example, in a biological analysis where a "scene," a field of view, or a portion of the sample has been stained with two dyes consisting of a marker dye for targeting the molecular specie of interest and a counterstain for staining the remainder of the sample.

In order to accurately measure the concentration of given species imaged under a microscope, the measurements of the optical densities performed at different wavelengths must specifically correspond to the observed portion of the sample. That is, the microscopy system must be corrected for chromatic aberration, wherein such a correction or compensation may be accomplished by hardware, software, or a combination of software and hardware. Generally, glass tends to disperse light, which typically causes, for example, a simple glass lens to focus blue light at a shorter distance than red light. That is, a simple glass lens will exhibit different focal lengths for light comprising different wavelengths. This dispersion characteristic of glass gives rise to two observed effects. First, longitudinal chromatic aberration, or the positional difference of the focal points for different wavelengths of light along the vertical axis, is observed where, upon focusing the image for selected wavelengths of light corresponding to a particular color, the image will tend to be slightly out of focus when viewed under wavelengths of light corresponding to other colors. For example, if the image is focused for one particular wavelength of light, the same image will tend to be out of focus when viewed under filters for a shorter or longer wavelength of light. Secondly, lateral chromatic aberration is observed as a difference in magnification for light of different wavelengths due to the different focal lengths thereof. For example, an image viewed under relatively short blue light wavelengths will appear larger than the same image viewed under relatively longer red light wavelengths.

In microscopy systems having high quality objectives such as, for instance, apochromatic objectives, a large portion of the apparent chromatic aberration may be corrected. However, some residual lateral chromatic aberration may still remain, resulting in differences in magnification across wavelengths of light. This lateral chromatic aberration may be difficult to visually observe since a human observer tends to concentrate on the center of the field of view where the lateral aberration is typically absent. However, when imaging the field of view using, for example, a CCD camera, a very small lateral chromatic aberration resulting in, for instance, even less than 1% difference in magnification between wavelengths, will result in slight color shifts about the edges of objects in the field of view, but located away for the optical center of the objective. Consequently, a pixel located at a given (x,y) position on the image may not exactly depict the corresponding portion of the object under investigation depending on the wavelength of light used to illuminate the object and the location of the object within the field of view. However, in order to solve chromogen separation equations derived from the Lambert-Beer law, a basic premise is that the exact same part of the object in the field of view must be examined. Therefore, images obtained for separate wavelengths of light must be adjusted to provide correlation with respect to the regions of the field of view where chromogen separation equations must be solved. Further, the plurality of images acquired from each of the scans of the object taken with respect to a specific wavelength should be scaled and aligned such that the pixels of an image captured at one wavelength correspond to pixels of an image captured at a different wavelength.

Accordingly, one advantageous aspect of the present invention involves a method of correcting lateral chromatic aberration within a microscopy system. First, the coordinates of the center of the magnifying objective 250 are determined with respect to the center of the electronic device or chip comprising the image-producing component of the camera 300. An observed magnification factor is then determined for each wavelength and compared to the magnification factor for an arbitrarily chosen wavelength. For example, a central wavelength would comprise the chosen wavelength to which the magnification factor for each of the other wavelengths would be compared. The image for each wavelength is then adjusted according to the determined relative magnification factor and the relative coordinates of the center of the magnifying objective 250.

In order to facilitate the steps of the described method, a specific calibration slide is used, wherein the slide is configured with a grid of regularly spaced fine holes through a light blocking media. An image of the grid is taken at each wavelength of light used to illuminate the sample. For example, an image may be produced for each of the wavelengths. The center of each hole is then computed in, for instance, x,y coordinates. The image corresponding to the wavelength of light nearest to the mean of the wavelengths of light under consideration is then designated as the reference image. Subsequently, each of the images for the other wavelengths under consideration is then compared to the reference image. For each hole in the grid, the difference in the x direction ($\delta x$) and the difference in the y direction ($\delta y$) are then determined for the corresponding hole in the reference image and the image being compared thereto. Equations such as, for example, linear equations that minimize the reconstruction error for $\delta x$ as a function of x and $\delta y$ as a function of y, are then determined. From these two equations, the center of the objective ($x_o, y_o$) is determined, where $x_o$ comprising the solution of the first equation in x when $\delta x$ is 0 and $y_o$ comprises the solution of the second equation in y when $\delta_y$ is 0. A linear equation that minimizes the reconstruction error of $\delta d$, where $\delta d = (\delta x^2 + \delta^2)^{1/2}$, as a function of the distance to the center of the objective is then determined, wherein the slope of that equation provides the magnification factor of the particular wavelength with respect to the reference wavelength. This image for the particular wavelength is then spatially adjusted such that the origin of the image corresponds to the center of the objective and the magnification of the image corresponds to the magnification of the reference image.

Another advantageous aspect of the present invention involves a method of aligning a plurality of images within a microscopy system. In one embodiment, a number of profiles are extracted from each of the plurality of images based on the background and object optical density. In order to extract the number of profiles, a binarized mask is generated from each of the images corresponding to the differing wavelengths. A binary mask for each image is created by first obtaining a shading-corrected image. In order to reduce high frequency noise artifacts, a low-pass filter may be applied to each of the plurality of shading-corrected images. A histogram detailing the background peak statistics is created from optical densities of the shading-corrected image. The histogram provides a background threshold used to create the binary mask, wherein a value less then or equal to the threshold is given a value of 0 and a value greater than the threshold is given a value of 1. From the binarized image, the horizontal and vertical profiles of the image are extracted, and the horizontal and vertical profiles of each of the images are then scaled according to the determined magnification factors. Once the profiles for each wavelength are adjusted according to the determined relative magnification factor, the profiles are evaluated to determine the actual shift between the profiles of a reference image corresponding to a reference wavelength and the profiles of the images for each of the other wavelengths. For further exemplary discussion regarding techniques for aligning a plurality of images of a sample within a microscopy system, see U.S. Patent Application No. 61/474,514, entitled METHOD FOR PREPARING QUANTITATIVE VIDEO-MICROSCOPY AND ASSOCIATED SYSTEM, which was filed on Apr. 12, 2011 and is incorporated in its entirety herein.

Once the microscope 150 has been configured to provide Köhler illumination for image acquisition and chromatic aberrations have been addressed, the additive property of the Lambert-Beer law can be applied to chromogen separation. For instance, the additive property of the Lambert-Beer law can be expanded to a situation in which the scene is analyzed in a black and white environment, generated by, for example, a black and white camera and a filter wheel having a number of wavelength filters or another device configured to filter light corresponding to specific wavelengths. Although one embodiment of the present invention may comprise a filter wheel having five wavelength filters, the present invention is not limited to 5 wavelengths, as the filter wheel or filtering device may have any number of wavelength filters corresponding to a desired number of dyes of interest. According to one embodiment, an image is acquired corresponding to each wavelength, and the images are analyzed on a per pixel basis at each corresponding pixel location, the images being carefully corrected for chromatic aberration and alignment across all wavelengths. Thus, a pixel at location x1,y1 located in image 1 is analyzed with respect to a corresponding pixel at location x1,y1 in images 2, 3, 4, 5, etc. Thus, the amounts of each molecular species at each corresponding pixel location may be determined for all of the pixels in the images.

In such an instance, a first dye exhibits absorption coefficients or spectral signature, $\epsilon_{11}$, $\epsilon_{12}$, $\epsilon_{13}$, $\epsilon_{14}$, and $\epsilon_{15}$, in the first through fifth wavelength filters, respectively. Accordingly, a second dye exhibits absorption coefficients, $\epsilon_{21}$, $\epsilon_{22}$, $\epsilon_{23}$, $\epsilon_{24}$, and $\epsilon_{25}$, in the first through fifth wavelengths, respectively. Therefore, according to the additive property of the Lambert-Beer law, analysis of the sample in the black and white environment leads to five equations for the optical density thereof:

$$OD_1 = \epsilon_{11} \cdot l_1 \cdot C_1 + \epsilon_{21} \cdot l_2 \cdot C_2 + \epsilon_{31} \cdot l_3 \cdot C_3 + \epsilon_{41} \cdot l_4 \cdot C_4 + \epsilon_{51} \cdot l_5 \cdot C_5 \quad (3)$$

$$OD_2 = \epsilon_{12} \cdot l_1 \cdot C_1 + \epsilon_{22} \cdot l_2 \cdot C_2 + \epsilon_{32} \cdot l_3 \cdot C_3 + \epsilon_{42} \cdot l_4 \cdot C_4 + \epsilon_{52} \cdot l_5 \cdot C_5 \quad (4)$$

$$OD_3 = \epsilon_{13} \cdot l_1 \cdot C_1 + \epsilon_{23} \cdot l_2 \cdot C_2 + \epsilon_{33} \cdot l_3 \cdot C_3 + \epsilon_{43} \cdot l_4 \cdot C_4 + \epsilon_{53} \cdot l_5 \cdot C_5 \quad (5)$$

$$OD_4 = \epsilon_{14} \cdot l_1 \cdot C_1 + \epsilon_{24} \cdot l_2 \cdot C_2 + \epsilon_{34} \cdot l_3 \cdot C_3 + \epsilon_{44} \cdot l_4 \cdot C_4 + \epsilon_{54} \cdot l_5 \cdot C_5 \quad (6)$$

$$OD_5 = \epsilon_{15} \cdot l_1 \cdot C_1 + \epsilon_{25} \cdot l_2 \cdot C_2 + \epsilon_{35} \cdot l_3 \cdot C_3 + \epsilon_{45} \cdot l_4 \cdot C_4 + \epsilon_{55} \cdot l_5 \cdot C_5 \quad (7)$$

where $OD_1$, $OD_2$, $OD_3$, $OD_4$ and $OD_5$ represent the optical densities of the sample measured for each of the wavelengths, respectively. It will be understood by one skilled in the art, however, that this demonstrated property of the Lambert-Beer law may be expanded to include an even greater plurality of dye combinations in accordance with the spirit and scope of the present invention. Note also that although the embodiment of this present invention utilizes a black and white imaging device having a plurality of wavelength filters for multi-spectral imaging of the dye markers over five distinct wavelengths, one skilled in the art will appreciate that the demonstrated concept may be applied to an imaging device capable of capturing an image over a plurality of wavelengths, and that the demonstrated concept may be applied to as many wavelength filters as are available with a particular imaging device, filter wheel, and/or other filtering device.

In applying the Lambert-Beer law to a digital microscopy system 100 according to embodiments of the present invention, it is difficult and complex, inaccurate, or sometimes not possible to measure the thickness l of the sample 500. In such instances, the concentration C of the molecular specie can be extended and examined as the product of l and C (l·C) and the results treated accordingly. For example, where the concentration of one dye is being compared to the concentration of another dye in a particular sample, the sample thickness term will be common to both concentrations and thus it becomes less important to determine the sample thickness as an absolute and accurate value. Accordingly, it will be understood by one skilled in the art that an accurate determination of the thickness of the sample is typically not required, but may generally be treated as a constant in examining the equations as detailed herein.

The application of the Lambert-Beer law to a digital microscopy system 100 of the present invention also recognizes that the Lambert-Beer law can also be expressed as:

$$OD_{(x,y)} = \log I_{0(x,y)} - \log I_{(x,y)} \quad (8)$$

for a digital image 450 of the sample 500 comprising a plurality of pixels arranged, for example, according to a Cartesian coordinate system, where (x,y) signifies a particular pixel in the image 450, $OD_{(x,y)}$ is the optical density of the sample 500 at that pixel, $I_{(x,y)}$ is the measured light intensity or transmittance of the sample 500 at that pixel, and $I_{0(x,y)}$ is the light intensity of the light source 200 as measured without any intermediate light-absorbing object, such as the sample. Accordingly:

$$IOD = \sum_N (\log I_{0(x,y)} - \log I_{(x,y)}) \quad (9)$$

where IOD is the integrated optical density of the digital image 450 of the sample 500, and N is the number of pixels in the surface image 450 of the sample. It will further be appreciated by one skilled in the art that the logarithmic relationship described in equations (8) and (9) may be expressed in various bases within the spirit and scope of the present invention. For example, the relationships may be expressed in base 2, base 10, or natural logarithms, wherein the various bases are related by respective proportionality constants (for example, $\ln(x)$ or $\log_e(x) = 2.3026 \log_{10}(x)$). Thus, the proportionality constant may be appropriately considered where relative comparisons are drawn in light intensities. Further, in quantitative microscopy according to the Lambert-Beer law, the proportionality relationship between the optical density OD of the sample and the dye concentrations is conserved.

Therefore, for a prepared sample 500 examined by the system 100, the appropriate relation is expressed as:

$$\ln I_0 - \ln I = \ln I_0/I = OD = \epsilon \cdot l \cdot C \quad (10)$$

Where, for example, a 16-bit black-and-white camera 300 is used in the system 100, the light intensity transmitted through the sample in each wavelength filter may be expressed as $2^{16}$ (=65536) values between 0 and 65535. For example, the initial intensity $I_o$ of the light source 200, which corresponds to 100% transmittance, will preferably be expressed in each of plurality of wavelengths as a value approaching 65535, representing the brightest possible value in each wavelength. The camera 300 and/or the light source 200 may be adjusted accordingly such that, in the absence of the sample, a pure "white" light will have an intensity value of 65535 in each of the wavelengths, corresponding to 100% transmittance. Conversely, in the absence of light, generally corresponding to transmittance approaching 0%, a "black image" will have an intensity value approaching 0 in each of the wavelengths. At any pixel, the initial intensity $I_o$ of the light source 200, corresponding to 100% transmittance, is therefore expressed as the difference between the value of the intensity measured in the presence of the light source 200 minus the value of the intensity measured in the absence of the light source 200 for each of the wavelength filters. Because the intensity of the light source 200 may vary spatially across the image 450, or over the measured field of view, and because the magnifying objective 250 or other optical components may heterogeneously absorb light, 100% transmittance may be represented by various differential intensities over the measured field of view. However, since the optical density OD of the sample is expressed as the logarithm of the ratio of light transmittance in absence of the sample (initial intensity $I_o$) to light transmittance in presence of the sample (I), the optical density OD is largely spatially insensitive to small variations in the differential intensities over the measured field of view.

Since the light source 200 remains substantially constant over time, or can be easily re-evaluated, the measurement of the light intensity for any pixel, in the presence of the sample, can be translated into the transmittance I at that pixel and in each of the wavelength filters. Once values for the initial intensity $I_o$ and transmittance I are determined, the optical density OD can be computed. As such, at any location in the field of view 450 where a unique dye is present, the absorption coefficient $\epsilon$ of that dye may be determined with respect to each of the wavelength filters. More particularly, $l \cdot C$ for a given pixel will be equal in each of the wavelength filters. Thus, if both l and C are known, the absorption coefficient $\epsilon$ can be computed according to equation (10) or in each of the wavelength filters as:

$$\epsilon_1 = OD_1/(l \cdot C) = (\ln(I_{o1}/I_1))/(l \cdot C) \quad (11)$$

$$\epsilon_2 = OD_2/(l \cdot C) = (\ln(I_{o2}/I_2))/(l \cdot C) \quad (12)$$

$$\epsilon_3 = OD_3/(l \cdot C) = (\ln(I_{o3}/I_3))/(l \cdot C) \quad (13)$$

$$\epsilon_4 = OD_4/(l \cdot C) = (\ln(I_{o4}/I_4))/(l \cdot C) \quad (14)$$

$$\epsilon_5 = OD_5/(l \cdot C) = (\ln(I_{o5}/I_5))/(l \cdot C) \quad (15)$$

However, $l \cdot C$ is typically not known for a particular pixel in an image of a particular sample. Therefore, the absorption coefficients $\epsilon$ are computed for each wavelength filter according to the ratio of the optical density OD in each wavelength filter, measured at a given pixel, to the maximum optical density OD out of all the wavelength filters measured at the same pixel. More particularly, it will be appreciated by one skilled in the art that the determination of the absorption coefficient $\epsilon$ in each of the wavelengths, in the absence of a priori knowledge of l and/or C, is a matter of manipulating the linear equations in order to achieve a relative solution where $l \cdot C$ is arbitrarily set to a value of 1, wherein:

$$\epsilon_1 = OD_1/1 = OD_1 = \ln(I_{o1}/I_1) \quad (16)$$

$$\epsilon_2 = OD_2/1 = OD_2 = \ln(I_{o2}/I_2) \quad (17)$$

$$\epsilon_3 = OD_3/1 = OD_3 = \ln(I_{o3}/I_3) \quad (18)$$

$$\epsilon_4 = OD_4/1 = OD_4 = \ln(I_{o4}/I_4) \quad (19)$$

$$\epsilon_5 = OD_5/1 = OD_5 = \ln(I_{o5}/I_5) \quad (20)$$

Consequently, if the absolute concentration of the particular dye remains unknown, a relative absorption coefficient $\epsilon$, for each of the wavelengths and for any given pixel, may be computed with an error factor equal to $l \cdot C$.

Alternatively, because l is unique at a given pixel location and can be arbitrarily set to a value of 1, equations (3-7) may be rewritten as follow where $C_1, C_2, C_3, C_4,$ and $C_5$ are related by a factor of 1:

$$OD_1 = \epsilon_{11} \cdot C_1 + \epsilon_{21} \cdot C_2 + \epsilon_{31} \cdot C_3 + \epsilon_{41} \cdot C_4 + \epsilon_{51} \cdot C_5 \quad (21)$$

$$OD_2 = \epsilon_{12} \cdot C_1 + \epsilon_{22} \cdot C_2 + \epsilon_{32} \cdot C_3 + \epsilon_{42} \cdot C_4 + \epsilon_{52} \cdot C_5 \quad (22)$$

$$OD_3 = \epsilon_{13} \cdot C_1 + \epsilon_{23} \cdot C_2 + \epsilon_{33} \cdot C_3 + \epsilon_{43} \cdot C_4 + \epsilon_{53} \cdot C_5 \quad (23)$$

$$OD_4 = \epsilon_{14} \cdot C_1 + \epsilon_{24} \cdot C_2 + \epsilon_{34} \cdot C_3 + \epsilon_{44} \cdot C_4 + \epsilon_{54} \cdot C_5 \quad (24)$$

$$OD_5 = \epsilon_{15} \cdot C_1 + \epsilon_{25} \cdot C_2 + \epsilon_{35} \cdot C_3 + \epsilon_{45} \cdot C_4 + \epsilon_{55} \cdot C_5 \quad (25)$$

Note that the determination of an absorption coefficient $\epsilon$ matrix for different dyes may be performed independently of sample evaluation and stored for further application to samples treated with at least one of the respective dyes. Further, the various absorption coefficient $\epsilon$ matrices for particular dyes, as well as the original light intensity $I_o$ data for the light source 200 may be stored in, for example, the computer device 350, a server located on an intranet or the Internet, or other data storage device as will be appreciated by one skilled in the art. As such, when absorption coefficients ε have been evaluated for the different dyes, and optical densities OD have been determined from image data, the appropriate equations may be solved as a set of linear equations so as to extract the respective concentrations of the dyes $C_1$, $C_2$, $C_3$, $C_4$ and $C_5$.

By way of further explanation, a representative set of linear algebraic equations may be, for example, expressed as:

$$a_{11}x_1+a_{12}x_2+a_{13}x_3+\ldots+a_{1N}x_N=b_1$$

$$a_{21}x_1+a_{22}x_2+a_{23}x_3+\ldots+a_{2N}x_N=b_2$$

$$a_{31}x_1+a_{32}x_2+a_{33}x_3+\ldots+a_{3N}x_N=b_3$$

$$\ldots$$

$$a_{M1}x_1+a_{M2}x_2+a_{M3}x_3+\ldots+a_{MN}x_N=b_M \quad (26)$$

where, for N unknowns, $x_j$, j=1, 2, ..., N are related by M equations. The coefficients $a_{ij}$, where i=1, 2, ... M and j=1, 2, ... N, are generally known, as are the quantities $b_i$, i=1, 2, ..., M. If M<N, there are effectively fewer equations than unknowns. In such a case, there can be either no solution or more than one solution matrix x. Further, if N=M, then there are as many equations as unknowns and a unique solution matrix x may likely be determined. In addition, if M>N, then there are more equations than unknowns and, in general, no particular solution matrix x to the set of equations. Accordingly, the set of equations is said to be over-determined and, in such a case, the most appropriate solution is generally considered to be the solution providing the best fit for the equations, wherein the best fit solution typically corresponds to the solution having the minimal sum of reconstruction errors.

Equation (26) may also be alternatively expressed as:

$$A \cdot x = b \quad (27)$$

where "·" denotes matrix multiplication, A is the matrix of coefficients, and b is the right side portion expressed as a column vector. Generally, by convention, the first index of an element $a_{ij}$ denotes the element row; while the second index denotes the element column. Further, $a_i$ or a[i] denotes an entire row a[i][j], j=1, ..., N. Accordingly, the solution of the matrix equation A·x=b for an unknown vector x, where A is the matrix of coefficients, and b is the right side portion, usually requires the determination of $A^{-1}$ or the matrix inverse of the matrix A. Thus:

$$x = A^{-1} \cdot b \quad (28)$$

Since $A^{-1}$ is the matrix inverse of matrix A, then $A \cdot A^{-1} = A^{-1} \cdot A = ID$, where ID is an identity matrix. To facilitate the determination of a solution, parameters may be established such that the number of equations is greater than or equal to the number of unknowns, or M≥N. As previously discussed, when M>N occurs there is, in general, no particular solution matrix x to equation (28) and the set of equations is over-determined. In such situations, however, the best "compromise" or best fit solution is often the solution that most closely and simultaneously satisfies all of the equations. Such closeness may be defined in, for example, a least-squares manner, wherein the sum of the squares of the differences between both sides of equation (28) is minimized. As a result, the over-determined set of linear equations may typically be reduced to a solvable linear problem, often referred to as a linear least-squares problem, that may be solved with singular value decomposition (SVD) mathematics as will be appreciated by one skilled in the art. SVD is directed to the parametric modeling of data and is usually the chosen method for solving linear least-squares problems and is described in further detail in, for example, NUMERICAL RECIPES IN C: THE ART OF SCIENTIFIC COMPUTING (ISBN 0-521-43108-5) Copyright © 1988-1992 by Cambridge University Press. Programs Copyright © 1988-1992 by Numerical Recipes Software.

The operation of the system 100 as described above may be further illustrated by example, assuming that the light source is a "white" light having $I_o$=65535 in each of the five wavelengths and that five dyes are used having the following transmitted light intensity I characteristics in each of the five wavelengths:

| I | | | | | |
|---|---|---|---|---|---|
| | Wavelength 1 | Wavelength 2 | Wavelength 3 | Wavelength 4 | Wavelength 5 |
| Dye 1 | 25264 | 27462 | 34245 | 45617 | 52728 |
| Dye 2 | 21979 | 35134 | 20320 | 53888 | 59097 |
| Dye 3 | 58224 | 60834 | 61183 | 54315 | 30280 |
| Dye 4 | 27570 | 19651 | 11411 | 10051 | 13679 |
| Dye 5 | 16066 | 11349 | 18845 | 44693 | 46263 |

The corresponding optical density OD matrix (each element being computed as $\ln(I_o/I)$) thus becomes:

| OD | | | | | |
|---|---|---|---|---|---|
| | Wavelength 1 | Wavelength 2 | Wavelength 3 | Wavelength 4 | Wavelength 5 |
| Dye 1 | 0.413960 | 0.377739 | 0.281866 | 0.157346 | 0.094424 |
| Dye 2 | 0.100639 | 0.270745 | 0.508536 | 0.084976 | 0.044904 |
| Dye 3 | 0.051369 | 0.032324 | 0.029842 | 0.081547 | 0.335308 |
| Dye 4 | 0.376025 | 0.523080 | 0.759134 | 0.814260 | 0.680395 |
| Dye 5 | 0.610557 | 0.761483 | 0.541262 | 0.166232 | 0.151231 |

However, since OD=ε·l·C, the OD values for each dye can be normalized with respect to the channel having the highest OD so as to provide a matrix of relative absorption coefficients ε for the respective dyes, since the l·C values will be constant across the wavelengths. Accordingly:

| ε | | | | | |
|---|---|---|---|---|---|
| | Wavelength 1 | Wavelength 2 | Wavelength 3 | Wavelength 4 | Wavelength 5 |
| Dye 1 | 1 | 0.9125 | 0.6809 | 0.3801 | 0.2281 |
| Dye 2 | 0.1979 | 0.5324 | 1 | 0.1671 | 0.0883 |
| Dye 3 | 0.1532 | 0.0964 | 0.089 | 0.2432 | 1 |
| Dye 4 | 0.4618 | 0.6424 | 0.9323 | 1 | 0.8356 |
| Dye 5 | 0.8018 | 1 | 0.7108 | 0.2183 | 0.1986 |

Subsequently, assuming that a sample 500 has been stained with the same five dyes, Dye 1, Dye 2, Dye 3, Dye 4 and Dye 5, and that a light source 200 with similar spectral characteristics is used to illuminate the sample 500, an image 450 of the sample 500 is captured by the camera 300 in each of the five wavelengths. At a particular pixel in the image 450, the computer device 350 then determines that the transmitted light intensity in each of the wavelengths is:

|   | Wavelength 1 | Wavelength 2 | Wavelength 3 | Wavelength 4 | Wavelength 5 |
|---|---|---|---|---|---|
| I | 33563 | 26985 | 20690 | 27531 | 25279 | where:

|   | Wavelength 1 | Wavelength 2 | Wavelength 3 | Wavelength 4 | Wavelength 5 |
|---|---|---|---|---|---|
| $I_o$ | 65535 | 65535 | 65535 | 65535 | 65535 |

Thus:

|   | Wavelength 1 | Wavelength 2 | Wavelength 3 | Wavelength 4 | Wavelength 5 |
|---|---|---|---|---|---|
| OD | 0.290607585 | 0.385346 | 0.500698 | 0.376643 | 0.41371 | for the particular pixel. Therefore, in order to determine the concentrations of the five dyes at that pixel, the OD matrix is multiplied by the inverse of the previously-determined relative absorption coefficient $\epsilon$ matrix ($(OD) \cdot \epsilon^{-1} = l \cdot C$). Accordingly:

|   | $l \cdot C$ (mole · cm/L) or $C_{relative}$ |
|---|---|
| Dye 1 | 0.068527 |
| Dye 2 | 0.14145 |
| Dye 3 | 0.139956 |
| Dye 4 | 0.281291 |
| Dye 5 | 0.053319 |

Further information regarding exemplary techniques for analyzing a sample using chromogen separation and Lambert-Beers law is detailed in U.S. Pat. No. 7,065,236 and U.S. Pat. No. 7,133,547, each to Marcelpoil et al. and assigned to the present assignee, and which are each incorporated by reference herein in their entirety.

Once an initial dye concentration vector C is evaluated, the refinement process 50 according to one embodiment of the present invention commences, as shown in FIG. 2. The initial dye concentration of a particular pixel is evaluated 6 and the number of dye concentrations present in a significant concentration, $N_s$, is identified and counted 7. In one embodiment of the present invention, the significant concentration, Ns, may be a concentration greater than 0.01. In another embodiment, the significant concentration, Ns, may be a concentration greater than the mean optical density background plus 6 times the standard deviation of the optical densities measured in the background. In one embodiment of the present invention, the refinement process 50 comprises five wavelength filters, wherein each wavelength filter corresponds to one of the five dye markers. If the number of dye concentrations present in a significant concentration, $N_s$, for a particular pixel is equal to the number of wavelength filters (i.e., $N_s=5$), the evaluated solution of the dye concentrations is kept, as no improvement or refinement can be made 62. Conversely, if the number of dye concentrations in present in a significant amount, $N_s$, for a particular pixel is one (i.e., $N_s=1$), the concentration of the sole dye is refined from the one particular wavelength that provides the maximum absorption peak.

Accordingly, the refinement and optimization process occurs when the number of dye concentrations, $N_s$, is between one and five (i.e., $N_s>1$ and $N_s<5$), according to the embodiment where five dyes are utilized. Thus, the refinement process may be implemented for a number of dyes that is greater than one but less than the maximum number of dyes in the sample. The total number of wavelength filter combinations is calculated 8, according to the binomial law. Specifically, the total number of possible subsets of $N_s$ wavelength filter combinations among N total wavelength filters is determined by equation (29).

$$\frac{N!}{N_s!(N-N_s)!} \quad (29)$$

One skilled in the art will appreciate that the refinement and optimization process may be applied for a system using a plurality of dye concentrations when the number of dye concentrations, $N_s$ present is greater than one and less than N−1, where N is equal to the total number of dye markers being used. Thus, in the present embodiment, when $N_s>1$ and $N_s<5$, the $N_s$ dye concentrations are refined using among all potential subsets of $N_s$ wavelengths.

According to one embodiment of the present invention, each possible subset of wavelength filter combinations is tested according to an optimality factor and the best solution, e.g., the wavelength filter combination from the subset of $N_s$ wavelengths that maximizes the optimality factor, is kept to refine the $N_s$ dye concentrations. The optimality factor is computed, in part, by calculating the wavelength combination specific extinction coefficient matrix E of the $N_s$ dyes and the transpose of the wavelength combination specific extinction coefficient matrix, $E^T$ 51. Specifically, the optimality factor is computed by calculating the Cayley-Menger Determinant of the wavelength combination specific extinction coefficient matrix and the transpose of the wavelength of wavelength specific extinction coefficient matrix 52. Once these determinants are obtained, the refinement process continues by multiplying the respective Cayley-Menger Determinants 53 to obtain a hypervolume. Further, the products of these Cayley-Menger Determinants for each of the wavelength filter combinations are compared 54 with one another in order to find the particular wavelength filter combination that provides the maximum product of the two determinants. The equation below illustrates the computation of the optimality factor evaluation $f(U_i)$.

$$f(U_i) = \text{CayleyMenger}(E_{ui}) \times \text{CaleyMenger}(E_{ui}^T) \quad (30)$$

By way of further explanation, the Cayley-Menger Determinant provides the volume of a simplex in j-dimensions. If S is a j-simplex in $R^n$ with vertices $v_1, \ldots, v_{j+1}$, and $B=(\beta_{ik})$ denotes the $(j+1) \times (j+1)$ matrix given by, $\beta_{ik}=|v_i-v_k|_2^2$, then the content, the hypervolume, $v_j$, is given by the following equation:

$$v_j^2(S) = \frac{(-1)^{j+1}}{2^j(j!)^2} \det(\hat{B}) \quad (31)$$

where $\hat{B}$ is the $(j+2) \times (j+2)$ matrix obtained from B by bordering B with a top row $(0, 1, \ldots, 1)$ and a left column $(0, 1, \ldots, 1)^T$. Here, the vector L2-norms $|v_i-v_k|_2$ (or vector norm) are the edge lengths and the determinant in equation (31) is the Cayley-Menger determinant (*An Introduction to the Geometry of n Dimensions*. Sommerville, D. M. Y. 1958; "On the Complexity of Some Basic Problems in Computational Convexity II, Volume and Mixed Volumes." *Polytopes:*

Abstract, Convex and Computational Gritzmann, P. and Klee, V. 1994.) The vector norm $|X|_p$ for p=1, 2, . . . is defined as $$|X|_p \equiv \left(\sum_i |x_i|^p\right)^{\frac{1}{p}}.$$

When p=2, the L2-norm is simply the vector norm or $|X|_2 = |X| = \sqrt{x_1^2 + x_2^2 + \ldots + x_n^2}$.

The first few coefficients for $$j = 0, 1, \ldots \quad \frac{(-1)^{j+1}}{2^j (j!)^2}$$

are −1, 2, 16, 288, −9216, 460800, . . . . (*On the Regular Heptagon*, Journal of Mathematical Chemistry, Alan L. Mackay, vol. 21, no. 2, pp. 197-209 (1997)). For j=2, the hypervolume is given as $$-16\Delta^2 = \begin{vmatrix} 0 & 1 & 1 & 1 \\ 1 & 0 & c^2 & b^2 \\ 1 & c^2 & 0 & a^2 \\ 1 & b^2 & a^2 & 0 \end{vmatrix} \quad (32)$$

The above-equation provides the area for a plane triangle with side lengths a, b, and c, and is a form of Heron's formula. For j=3, the content of the 3-simplex is given by the determinant $$288v^2 = \begin{vmatrix} 0 & 1 & 1 & 1 & 1 \\ 1 & 0 & d_{12}^2 & d_{13}^2 & d_{14}^2 \\ 1 & d_{21}^2 & 0 & d_{23}^2 & d_{24}^2 \\ 1 & d_{31}^2 & d_{32}^2 & 0 & d_{34}^2 \\ 1 & d_{41}^2 & d_{42}^2 & d_{43}^2 & 0 \end{vmatrix} \quad (33)$$

where the edge between vertices i and j has a length of $d_{ij}$.

A general determinant for a matrix A has a value $$|A| = \sum_{i=1}^{k} a_{ij} C_{ij}$$

with no implied summation over j and where $C_{ij}$ is the cofactor of $a_{ij}$ defined by $C_{ij} = (-1)^{i+j} M_{ij}$, and $M_{ij}$ is the minor matrix of A formed by eliminating row i and column j from A. This process is also called determinant expansion by minors or Laplacian expansion by minors. More particularly, a k×k determinant can be expanded by "minors" to obtain:

$$\begin{vmatrix} a_{11} & a_{12} & a_{13} & \ldots & a_{1k} \\ a_{21} & a_{22} & a_{23} & \ldots & a_{2k} \\ \vdots & \vdots & \vdots & \ddots & \vdots \\ a_{k1} & a_{k2} & a_{k3} & \ldots & a_{kk} \end{vmatrix} = a_{11} \begin{vmatrix} a_{22} & a_{23} & \ldots & a_{2k} \\ \vdots & \vdots & \ddots & \vdots \\ a_{k2} & a_{k3} & \ldots & a_{kk} \end{vmatrix} - \quad (34)$$

-continued $$a_{12} \begin{vmatrix} a_{21} & a_{23} & \ldots & a_{2k} \\ \vdots & \vdots & \ddots & \vdots \\ a_{k1} & a_{k3} & \ldots & a_{kk} \end{vmatrix} + \ldots \pm a_{1k} \begin{vmatrix} a_{21} & a_{22} & \ldots & a_{2(k-1)} \\ \vdots & \vdots & \ddots & \vdots \\ a_{k1} & a_{k2} & \ldots & a_{k(k-1)} \end{vmatrix}$$

As stated previously, the optimal wavelength filter combination, $U_{opt}$, is defined by the maximum product of the Cayley-Menger Determinant of the wavelength combination specific extinction coefficient matrix and the Cayley-Menger Determinant of the transpose of the wavelength combination specific extinction coefficient matrix. Specifically, the optimal wavelength filter combination, $U_{opt}$, is determined by calculating the product of the two Cayley-Menger Determinants for each wavelength filter combination, as shown in the equation below.

$$f(U_{opt}) = \max[f(U_i)]_{i=1}^{i=\frac{N!}{N_s!(N-N_s)!}} \quad (35)$$

According to one embodiment of the present invention, a refined estimation of the dye concentrations, $C_{Ns}$ is computed once the optimal wavelength filter combination, $U_{opt}$, is determined. The refined estimation of the dye concentrations, $C_{Ns}$ is calculated from the multi-spectral optical densities input vector, $OD_{Ns}$ and the inverse of the dye extinction coefficient matrix, $E_{Ns}^{-1}$, which is a square matrix having $N_s$ rows and $N_s$ columns, as shown in the equation below, and as shown as element 60 in FIG. 2.

$$C_{Ns} = E_{U_{opt}}^{-1} \cdot OD_{Ns} \quad (36)$$

Specifically, the refined estimation of the dye concentrations, $C_{Ns}$, is computed from the multi-spectral optical densities input vector, $OD_{Ns}$, and the inverse of the dye extinction coefficient matrix, $E_{Ns}^{-1}$, that relate to the specific wavelength combination that provided the greatest product of the two Cayley-Menger Determinants from equation (30).

According to the methodology described herein, the refined dye concentrations may then be used to reconstruct a refined artificial image of the sample. The artificial images may be generated as a substantially real time or live image, or as a still image, using combinations of the dyes comprising a marker and/or a counterstain used to prepare the sample. More particularly, an artificial image of the field of view may be produced which shows the sample as affected by all of the dyes, the sample as affected by one or more marker dyes, or the sample as affected by the counterstain. Consequently, since the dyes used to prepare the sample are characterized by the system, the capabilities of the system may be extended such that, for instance, the sample or field of view may be automatically scanned to detect a specific region of interest as identified by the characteristics of a particular dye or to affect or facilitate a task to be performed on that specific region of interest.

Still further, the artificial image of the field of view may also be used to facilitate the identification and extraction of selected features of the treated sample. For example, marked point processes, contextual analysis, and/or geo-statistics may be used to identify and extract features from the image based on, for instance, a spatial distribution analysis of a particular dye. Such a feature extraction capability would also allow, for example, fields of view or objects of interest to be sorted, flagged, or otherwise identified or grouped based on, for instance, the overall content of a given marker dye or a selected ratio of particular marker. Where, for example, a threshold criteria can be established, such a capability would be the detection of rare, worsening, or other serious events. Proceeding further, classifiers based specifically on the image processing resulting from the counterstain and/or marker dye specific images may then be established and used to evaluate the presence of certain cell types or to perform a diagnosis based upon the field of view. For example, HER2 may be evaluated in this manner by comparison to a continuous diagnosis scale established according to the system and methods described herein. Such classifiers may usually also encompass other informative features such as, for example, detail based upon the morphology or the texture of the cells.

It will be understood that the methodology and procedures detailed herein in conjunction with the system 100 specify a method of determining and refining an amount of a molecular specie from an image of a sample captured by an image-acquisition device in a video-microscopy system. One skilled in the art will also appreciate that such a method may be automated so as to provide a computer software program product, executable on a computer device, having executable portions capable of quantifying the amount of a molecular specie from a digital image of a sample captured by an image-acquisition device, such as a camera or scanner, in a video-microscopy system. Accordingly, embodiments of the present invention describe the implementation of a method and/or corresponding computer software program product which may be accomplished in appropriately configured hardware, software, or a combination of hardware and software in accordance with the scope of the present invention.

Thus, embodiments of the present invention comprise a refined colorimetric analysis technique for prepared samples that may provide effective detection and quantification of species of interest that overcomes limiting factors of prior art technologies, such as errors in dye concentration estimations due to noise fluctuations and/or global noise. Embodiments of the present invention further may provide more accurate estimations of dye concentrations of each corresponding pixel location of the plurality of images of the sample so as to optimize the amounts of those molecular species indicated in the images. Embodiments of the present invention further may provide an image processing technique which does not rely upon the subjective detection of a molecular species. Therefore, embodiments of the present invention provide a simpler and more effective analysis technique that is capable of providing the necessary analysis information about the sample, once an image of the sample is captured, without relying upon further examination of the sample to complete the analysis.

Moreover, the analysis of the prepared sample is accomplished using digital images of the sample. Since the analysis is relatively image-dependent, rather than sample-dependent, redundant images may be captured for analysis, while many samples may be processed so as to capture the necessary images within a relatively short period of time. Once the image data has been captured and stored, the actual analysis may occur at a later time or as needed without requiring the physical presence of the actual sample. Such an analysis may be further applied to examining the entire sample or even the entire slide. Thus, embodiments of the present invention may provide an expeditious quantitative video-microscopy system with a relatively high analysis throughput.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for determining an amount of a plurality of molecular species in a sample, each molecular specie being indicated by a dye, said method comprising:
    acquiring a plurality of images of the sample using an image acquisition device;
    determining an amount of each molecular specie, as indicated by a respective dye, for each pixel at each corresponding pixel location in the plurality of images, using a processor in communication with the image acquisition device; and
    refining the amount of a plurality of molecular species at one or more pixel locations in the plurality of images,
    wherein refining comprises determining an amount of dye concentrations that are present in the sample in a significant amount, determining a number of subsets of wavelength filter combinations, testing each of the subsets of wavelength filter combinations according to an optimality factor, and determining an optimal wavelength filter combination, and
    wherein testing each subset of wavelength filter combinations comprises multiplying a hypervolume of an absorption coefficient matrix and a hypervolume of a transpose of the absorption coefficient matrix specific to a particular subset of wavelength filter combinations.

2. A method according to claim 1, wherein determining comprises determining the concentration of a dye present in each pixel at each corresponding pixel location.

3. A method according to claim 2, wherein refining further comprises determining each molecular species comprising a significant concentration, and wherein refining comprises refining the concentration for a plurality of molecular species having a significant concentration at one or more pixel locations in the plurality of images.

4. A method according to claim 1, wherein acquiring a plurality of images of the sample comprises acquiring the plurality of images with a video-microscopy system.

5. A method according to claim 1, wherein determining an amount of each molecular specie comprises:
    determining an optical density of each dye so as to form a corresponding optical density matrix for each pixel at each corresponding pixel location;
    determining a relative absorption coefficient of each dye, determined independently of the sample, so as to form a relative absorption coefficient matrix for each pixel at each corresponding pixel location; and
    multiplying the optical density matrix by an inverse of a relative absorption
    coefficient matrix so as to form a resultant matrix for each pixel location, the resultant matrix comprising the amount of each molecular specie, as indicated by the respective dye, for each pixel location.

6. A method according to claim 1, wherein refining comprises determining a hypervolume of a simplex corresponding to the plurality of molecular species.

7. A method according to claim 1, wherein refining comprises determining a plurality of subsets of wavelength filter combinations corresponding to the plurality of molecular species.

8. A method according to claim 1, wherein each subset of wavelength filter combinations comprises a number of wavelength filters equal to the number of dye concentrations that are present in the sample in a significant amount.

9. A method according to claim 1, wherein refining the amount of each molecular specie further comprises:
   determining an optimized optical density matrix for each pixel location;
   determining an optimized relative absorption coefficient matrix; and
   multiplying the optimized optical density matrix by an inverse of the optimized relative absorption coefficient matrix so as to form an optimized dye concentration matrix for each pixel location, the optimized dye concentration matrix comprising the amount of each molecular specie, as indicated by the respective dye, for each pixel location.

10. A method according to claim 1, wherein the optimal wavelength filter combination is the wavelength filter combination that provides a maximum value of the product of the two hypervolumes.

11. A method according to claim 1, wherein testing each of the subsets of wavelength filter combinations further comprises:
   determining a Cayley-Menger Determinant of each of an absorption coefficient matrix and a transpose of the absorption coefficient matrix specific to a particular combination of wavelength filters; and
   multiplying the Cayley-Menger Determinant of the absorption coefficient matrix to a particular combination of wavelength filters and the Cayley-Menger Determinant of the transpose of the absorption coefficient matrix to a particular combination of wavelength filters.

12. A method according to claim 11, wherein the optimal wavelength filter combination is the wavelength filter combination that provides a maximum value of the product of the Cayley-Menger Determinant of the absorption coefficient matrix to a particular combination of wavelength filters and the Cayley-Menger Determinant of the transpose of the absorption coefficient matrix to a particular combination of wavelength filters.

13. A video-microscopy system for determining an amount of a plurality of molecular species in a sample, each molecular specie being indicated by a dye, from a plurality of images of the sample, said system comprising:
   an image acquisition device configured to capture a plurality of magnified digital image of the sample;
   a processor device in communication with the image acquisition device and configured to:
      determine an amount of each molecular specie, as indicated by a respective dye, for each pixel at each corresponding pixel location in the plurality of images;
      refine the amount of a plurality of molecular species at one or more pixel locations in the plurality of images;
      determine a hypervolume of an absorption coefficient matrix specific to a particular combination of wavelength filters; and
      determine a hypervolume of a transpose of the absorption coefficient matrix specific to a particular combination of wavelength filters.

14. A system according to claim 13, wherein the processor device is further configured to:
   determine an optical density of the sample, in each of a plurality of wavelengths and for a pixel in the image, so as to form a corresponding optical density matrix for each pixel at each corresponding pixel location;
   determine a relative absorption coefficient for the dye indicating each molecular specie, independently of the sample and in each of the plurality of wavelengths, so as to form a corresponding relative absorption coefficient matrix; and
   multiply the optical density matrix by an inverse of the relative absorption coefficient matrix so as to form a dye concentration matrix for each pixel location, the dye concentration matrix comprising the amount of each molecular specie, as indicated by the respective dye for each pixel location.

15. A system according to claim 13, wherein the amount of a plurality of molecular species is determined by the concentration of a dye present at a corresponding pixel location.

16. A system according to claim 13, wherein the image acquisition device comprises a black and white camera.

17. A system according to claim 13, wherein the image acquisition device comprises a plurality of filters, each filter corresponding to a different wavelength representative of a respective dye in the sample.

18. A system according to claim 13, wherein the processor device is further configured to determine the concentration of a dye present in each pixel at each corresponding pixel location.

19. A system according to claim 18, wherein the processor device is configured to determine each molecular species comprising a significant concentration and to refine the concentration for a plurality of molecular species having a significant concentration at one or more pixel locations in the plurality of images.

20. A system according to claim 13, wherein the processor device is further configured to:
   determine a number of subset of wavelength filter combinations, wherein each subset of wavelength filter combinations comprises a number of wavelength filters equal to the number of dye concentrations that are present in the molecular specie in a significant amount;
   test each subset of wavelength filter combinations according to an optimality factor; and
   determine an optimal wavelength filter combination.

21. A system according to claim 13, wherein the processor device is further configured to determine the maximum product of the two hypervolumes for each subset of wavelength filter combination.

22. A system according to claim 13, wherein the processor device is further configured to:
   determine a Cayley-Menger Determinant of each of an absorption coefficient matrix and a transpose of the absorption coefficient matrix specific to a particular combination of wavelength filters; and
   multiply the Cayley-Menger Determinant of the absorption coefficient matrix and the Cayley-Menger Determinant of the transpose of the absorption coefficient matrix specific to a particular combination of wavelength filters.

23. A system according to claim 22, wherein the processor device is further configured to determine the maximum product of the Cayley-Menger Determinant of the absorption coefficient matrix and the Cayley-Menger Determinant of the transpose of the absorption coefficient matrix for each subset of wavelength filter combination.

24. A system according to claim 13, wherein the processor device is further configured to determine a hypervolume of a simplex corresponding to the plurality of molecular species.

25. A system according to claim 13, wherein the processor device is further configured to determine a plurality of subsets of wavelength filter combinations corresponding to the plurality of molecular species.

* * * * *